US005468212A

United States Patent [19]
Shooter

[11] Patent Number: 5,468,212
[45] Date of Patent: Nov. 21, 1995

[54] DEVICE FOR CONTROLLING PREMATURE EJACULATION

[76] Inventor: Ernest K. Shooter, 44 Musgrave Road, Durban 4001, South Africa

[21] Appl. No.: 281,636

[22] Filed: Jul. 28, 1994

[30] Foreign Application Priority Data

Jan. 24, 1994 [ZA] South Africa ............................. 94/0471

[51] Int. Cl.$^6$ ..................................................... A61F 5/00
[52] U.S. Cl. ................................................ 600/39; 600/41
[58] Field of Search ................................. 600/38–39, 41

[56] References Cited

U.S. PATENT DOCUMENTS

| | | | |
|---|---|---|---|
| 837,993 | 12/1906 | Williams | 600/39 |
| 3,920,007 | 11/1975 | Line | 600/39 |
| 3,939,827 | 2/1976 | Brunstetter | 600/39 |
| 4,224,933 | 9/1980 | Reiling | 600/39 |
| 4,381,000 | 4/1983 | Duncan | 600/39 |
| 5,063,915 | 11/1991 | Wyckoff | 600/38 |
| 5,244,453 | 9/1993 | Osbon et al. | 600/38 |
| 5,327,910 | 7/1994 | Flynn | 600/38 |

FOREIGN PATENT DOCUMENTS

| | | | |
|---|---|---|---|
| 2355495 | 1/1978 | France | 600/39 |
| 1715344 | 2/1992 | U.S.S.R. | 600/39 |
| 0547535 | 9/1942 | United Kingdom | 600/39 |

*Primary Examiner*—Angela D. Sykes
*Attorney, Agent, or Firm*—Young & Thompson

[57] ABSTRACT

A device for preventing premature ejaculation during sexual intercourse includes a convex saddle with flanges of rubber at front and rear, the flanges having a flexibility sufficient for it to be removably located on the penis and hard enough to provide the same or similar texture and feel of the penile surface, the front flange of the device being shaped complementally to the rear of the glans, and having an elasticity for imparting a sufficient inward pressure to control premature ejaculation.

3 Claims, 2 Drawing Sheets

DEVICE FOR CONTROLLING PREMATURE EJACULATION

FIELD OF THE INVENTION

This invention relates to a device for controlling premature ejaculation and for assisting men to attain a satisfactory erection for the sexual act; and to hold a condom securely in place.

BACKGROUND OF THE INVENTION

Sexual impotence among men has long been the subject of investigation and a number of causes have been established. These include the obvious ones of mental and physical strain, emotional stress, smoking and the most common of all, age, with approximately fifty percent of all men older than forty suffering at least some degree of impotence. Impotence may also be induced by illness or even as a side effect of certain prescribed medicines.

Prior art inventions designed to stimulate and maintain a penile erection are varied and numerous. U.S. Pat. No. 4,665,902 and WO 9321872 describe a prosthesis for implantation into a penis.

The disadvantages of such internal, surgically implanted supports in everyday life are obvious and consequently efforts have been re-focussed on the provision of external aids.

German Patent DE 4129173 and DE 4227150 as well as WO 9004368 essentially involve a restriction of the blood flow from an erect penis and in so doing purport to extend the duration of an erection.

While these inventions do offer improvements over previous tourniquet models, it is clear that the numbness and soreness associated therewith has not entirely been obviated.

External penile supports in the form of a sleeve have a number of disadvantages. Jaegle's invention (DE 4225160), like that described in U.S. Pat. No. 2,868,192 comprises a support tube which must be threaded over the penis, with difficulty. Neither invention provides for increased potency on the male's part and they should rather be viewed as sex aids than aids to impotence or premature ejaculation.

GB 2 259 017 (Ford) describes a support comprising a shaped cover which fits over the penis and is held in position by a condom. This has the advantage of allowing some stimulation to the underside of the penis as well as preventing sexually transmitted diseases. It does not however assist with impotence or premature ejaculation.

EP 536598 also involves an elastic tubular support, but which is open-ended and is narrowed from base to tip to aid impotency. Problems are envisaged with insertion of the penis.

Immonen in GB 2208151 describes a split tubular member shaped anatomically to fit into the neck of the glans of the penis. This structure however must be held in place by bindings or adhesive strips which are likely to come off or to cause irritation to the vagina. This may be rectified by the use of a condom, although no provision is made for its retention in the desired location. In addition the surface area of the penis exposed to stimulation by the vagina is limited.

It is clear that many devices have been proposed to assist or simulate an erection but none of these has been successful enough to be universally enjoyed. It is an object of the present invention to provide a device which is easy to use, effective and which is inexpensive to produce. A further object is to permit safe use without the risk of contracting of sexually transmitted diseases as well as to control premature ejaculation. A yet further object is to hold a condom securely in place.

THE SUMMARY OF INVENTION

A device for controlling premature ejaculation including a convex saddle with front and rear flanges of rubber or rubber-like material having a flexibility sufficient for it to be removably located on a penis and hard enough to provide the same or similar texture and feel of the penile surface, and being positionable with one end fitting behind the glans and the other end against the pubic bone; and the end fitting behind the glans being adaptable to provide a predetermined inward pressure sufficient to control premature ejaculation.

In a preferred form of the invention the device is designed so that the maximum area of natural penile surface is available.

The flexibility of the material may be chosen so that the device is firmly held in position as well as imparting a predetermined inward pressure at the back of the glans—thereby helping to control premature ejaculation.

The degree of inward pressure may be reduced by cutting or the like, the flanges, thereby losing their inward pressure accordingly. Alternatively, the devices of the invention may be presented with varying thickness, dimensions or materials to provide varying inward pressure according to choice of the customers.

Although the device may have a resiliency which enables it to be firmly located it is better to provide a form of anchorage and for this purpose grooves may be provided to receive a condom or elastic band/s.

The device of the invention may be adapted to assist, simulate or artificially produce a penile erection by choosing a suitable material which has sufficient longitudinal rigidity.

The device may be provided with grooves in the zone adjacent the pubic bone for anchorage of the rim of the condom.

BRIEF DESCRIPTION OF THE DRAWINGS

Embodiments of the invention are described below with reference to the accompanying drawings in which.

DESCRIPTION OF THE PREFERRED EMBODIMENTS

In FIGS. 1 through 4, a device is shown which is adapted to be used in conjunction with a condom. The device comprises a convex saddle 10 which sits on the upper surface of the shaft of a semi-erect penis, extending from the rear of the glans to the front of the pubic bone, above the scrotum. The saddle supports flanges 11 and 13 at the front and back thereof respectively. The front flanges are shaped to fit snugly behind the glans while the rear ones are straight.

The device is of a rubber-like material with sufficient flexibility to allow location on a partially erect penis but with sufficient rigidity for intercourse. The material of construction should also facilitate a predetermined pinching effect to maintain the position of the device on the penis and to help control premature ejaculation.

Figure 1:
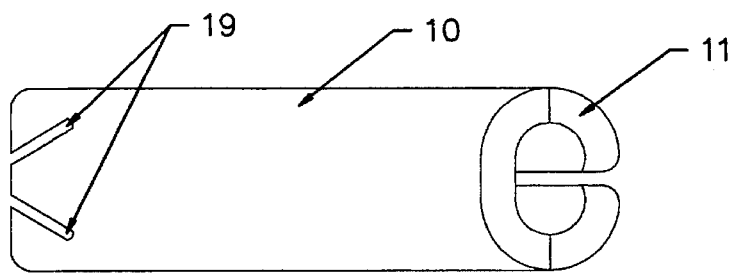
FIG. 1 is a top view of a device according to the invention.
Figure 2:
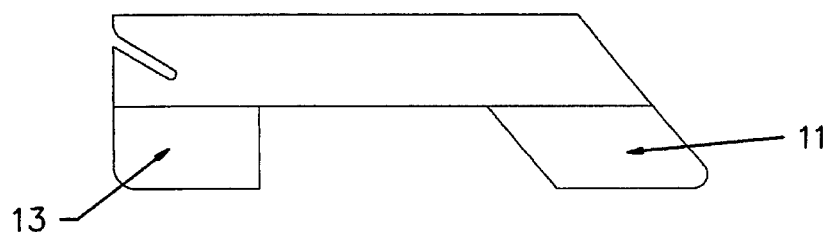
FIG. 2 is a side view of FIG. 1.
Figure 3:
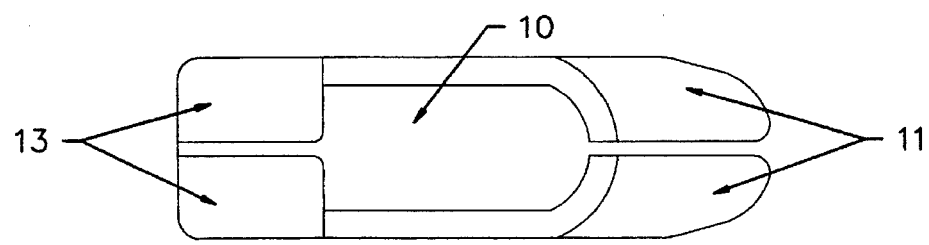
FIG. 3 is a bottom view of the device.
Figure 4:
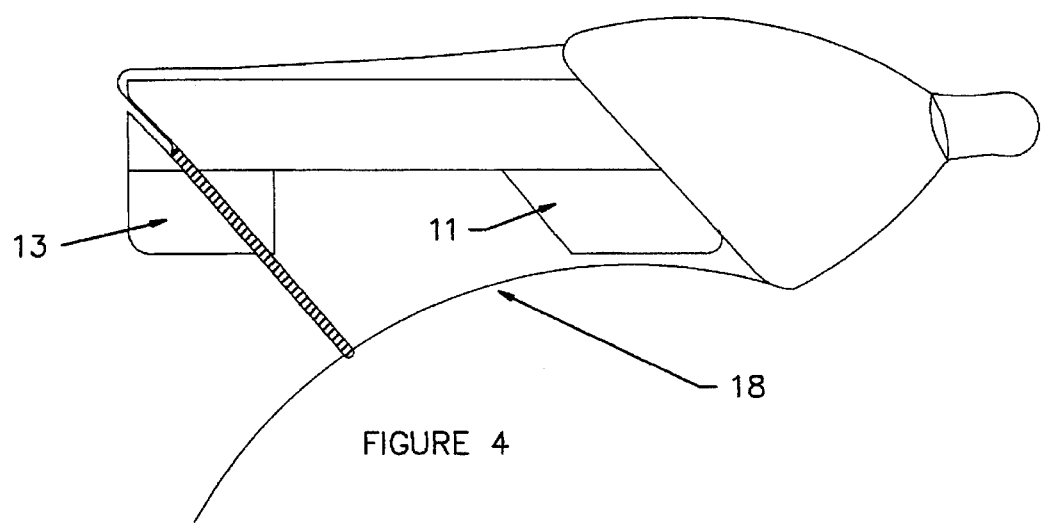
FIG. 4 is a side view of the device held in place by a condom.

In order to ensure that the device is firmly located, a form of anchorage should also be provided. For this purpose grooves 19 are provided into which the open end of a condom is fitted. Once the device and the condom are in position, the elasticity of the condom 18 provides the sought after anchorage as shown in FIG. 4.

Figure 5:
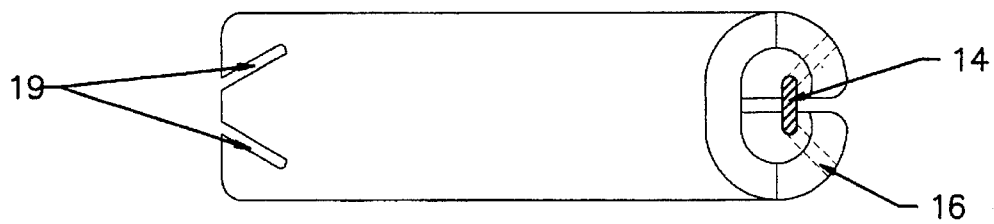
FIG. 5 is a top view of an alternative form of the invention.
Figure 6:
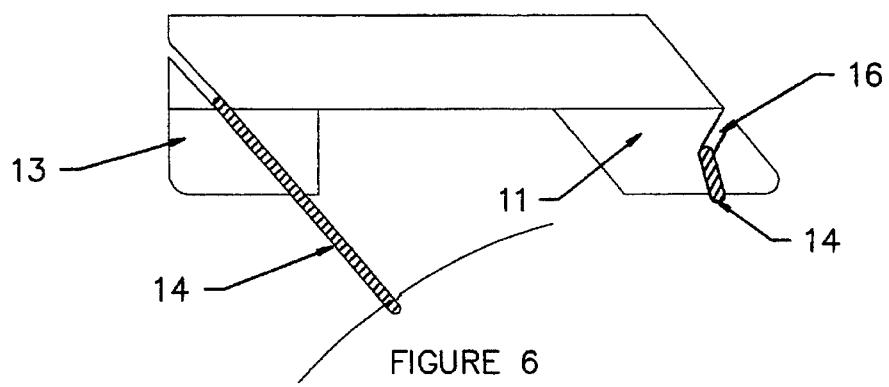
FIG. 6 is a side view of the device of FIG. 5.
Figure 7:
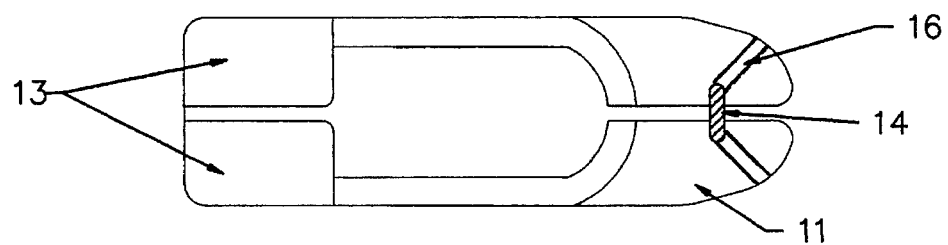
FIG. 7 is a bottom view of FIG. 6.

Turning to FIGS. 5 through 7, an an alternative form of the device is shown in which the additional anchorage is provided by elastic bands only. This form of the invention includes grooves at the front end 16 thereof as well as at the back end 19 so that the device is anchored by elastic bands 14 at both ends.

The object of the device shown in FIGS. 5 to 7 is that it can be used without a condom whereas the arrangement of FIGS. 1 to 4 requires a condom. However, greater care must be taken during penetration. Naturally a greater sensitivity is obtained.

The device shown in FIGS. 1 to 4 should always be used in the beginning until proficiency is obtained.

Figure 8:
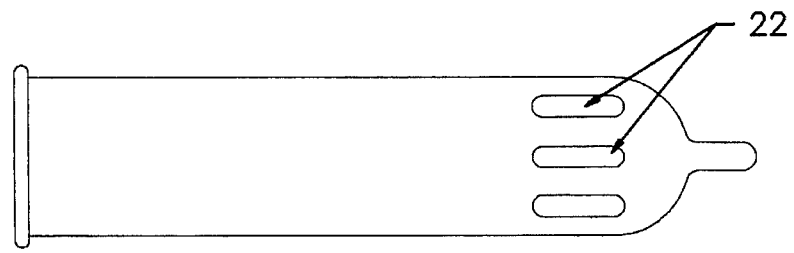
FIG. 8 is a top view of a cut-away condom.

A condom with cut-aways 22 may be used (see FIG. 8) with the device where the condom covers the device but not the complete glans. This will keep the device effectively in pace while allowing greater sensitivity.

I claim:

1. A device for controlling premature ejaculation comprising: a tubular member having a longitudinal axis, and extending in the direction of said longitudinal axis from a first end to an opposite second end; said tubular member having an external surface which generally extends in a rotational direction relative to said longitudinal axis from a first edge to an opposite second edge; said first edge being spaced from said second edge in said rotational direction, for the length of said tubular member from said first end to said opposite second end, to form an opening between said first edge and said second edge; a first length of said opening adjacent said first end and a second length of said opening adjacent said second end, each of said first length and second length having a width which is substantially smaller than a third length of said opening intermediate of and extending between said first length and said second length; said tubular member being sufficiently flexible for it to be removably located on a penis and hard enough to provide a texture and feel similar to that of the surface of the penis; and a first portion of said tubular member adjacent said first end and said first length forming a front flange having an edge which is shaped complementally to the rear of the glans of the penis, and having an elasticity for imparting a sufficient inward pressure to control premature ejaculation.

2. A device according to claim 1, wherein a second portion of said tubular member adjacent said second end and said second length includes slots for receiving a condom.

3. A device according to claim 1, wherein the tubular member comprises a material having a longitudinal rigidity sufficient for assisting, simulating or artificially producing a penile erection.

* * * * *